United States Patent [19]

Besnainou et al.

[11] Patent Number: 4,918,013

[45] Date of Patent: Apr. 17, 1990

[54] METHOD FOR PRODUCING PYRUVIC ACID BY FERMENTATION

[75] Inventors: Bernard Besnainou, Aix En Provence; Dominique Giani, Peronne; Claire Sahut, Aix En Provence, all of France

[73] Assignee: Commissariat a l'Energie Atomique, Paris, France

[21] Appl. No.: 258,391

[22] Filed: Oct. 17, 1988

[30] Foreign Application Priority Data

Oct. 15, 1987 [FR] France ................... 87 14248

[51] Int. Cl.[4] .................... C12P 7/40; C12R 1/72; C12R 1/73
[52] U.S. Cl. ......................... 435/136; 435/923
[58] Field of Search .................... 435/136, 923

[56] References Cited

U.S. PATENT DOCUMENTS 3,993,543 11/1976 Uchio et al. ............... 435/136

FOREIGN PATENT DOCUMENTS 2278890 2/1976 France .
1012293 1/1986 Japan .................... 435/136
1227789 10/1986 Japan .................... 435/136
0636262 12/1978 U.S.S.R. ................. 435/136

OTHER PUBLICATIONS

CHEMICAL ABSTRACTS, vol. 68, No. 23, Jun. 3, 1968, p. 9920, No. 102810k, Columbus, Ohio; T. V. Finogenova et al.: KETO ACID PRODUCTION BY PARAFFINOXIDIZING YEASTS.
CHEMICAL ABSTRACTS, vol. 84, No. 25, Jun. 21, 1976, p. 420, No. 178212t, Columbus, Ohio.

*Primary Examiner*—Herbert J. Lilling
*Attorney, Agent, or Firm*—Pearne, Gordon, McCoy & Granger

[57] ABSTRACT

The present invention relates to a method for producing pyruvic acid.

This method consists of first producing Candida type cells at approximately 5 pH by using a culture medium comprising thiamine and then producing pyruvic acid by culturing cells at about 4 pH by using a culture medium not containing thiamine or iron. Therefore, the production of pyruvic acid (curve I) is favored by limiting the production of alpha-ketoglutaric acid (curve II).

13 Claims, 2 Drawing Sheets

METHOD FOR PRODUCING PYRUVIC ACID BY FERMENTATION

FIELD OF THE INVENTION

The present invention relates to a method for preparing pyruvic acid by fermentation, more particularly fermentation by means of using Candida type yeast.

BACKGROUND OF THE INVENTION

The pyruvic acid is a starting material favorizing the preparation of essential amino acids, such as tryptophane, tyrosine or alanine. It is a compound which also has the advantage of being used as an additive conferring an acidulous flavor.

It is known that the culture of yeasts such as those of the Candida type results in pyruvic acid being produced in the culture medium. However, The amount of pyruvic acids produced in such conditions is small and it is difficult to envisage this production to be realized on an industrial scale owing to its low yield.

It is known by means of the method of the French patent FR-A-2 277 890 on how to produce pyruvic acid by fermentation, which makes it possible to increase the yield of pyruvic acid by using special yeasts which are Candida type mutants requiring thiamine and methionine for their growth.

This method therefore has the drawback of requiring the use of special yeast branches.

SUMMARY OF THE INVENTION

The main object of the present invention is to provide a method to produce pyruvic acid and which can be used on an industrial scale with a higher yield not requiring mutated branches and which makes it possible to limit the simultaneous production of alpha-ketoglutaric acid.

According to the invention, the method for producing pyruvic acid by fermentation consists of:

1.—cultivating Candida type cells in a culture medium comprising a carbon source, a nitrogen source, thiamine and mineral salts at a pH of 4.5 to 5.5 in aerobic conditions.

2.—separating the cells thus produced from the growth medium,

3.—cultivating these cells in a bioconversion medium containing a carbon source and mineral elements at a pH of 3.5 to 4.5 in aerobic conditions, and 4.—extracting from the culture medium the pyruvic acid product.

In the third stage of this method, the choice of a pH of from 3.5 to 4.5, preferably about 4, favors the production of pyruvic acid to the detriment of alpha-ketoglutaric acid.

Moreover, the choice of this pH range and a bioconversion medium, which preferably does not contain thiamine and iron, allows for this culture to be produced without increasing the biomass, and to thus convert most of the carbon introduced into the culture medium into advantageously useful products, such as pyruvic acid.

Preferably and so as to obtain a high yield of pyruvic acid, the cells concentration of the bioconversion medium must be at least 5 g/l at the start of the culture.

The culture medium used in this invention is a conventional medium enabling pyruvic acid to be produced. Accordingly, it contains sources of assimilable carbon and inorganic salts.

The carbon sources may be saccharides, such as glucose, fructose, suchrose and starch hydrolyzates. For reasons of cost, starch hydrolyzates are preferably used.

The inorganic salts generally used in the culture medium are Fe, K, Na, Mg, Mn, N, P, and S salts, namely those required for enzymatical syntheses allowing for the biomass to be increased.

Preferably and so as to favor the production of pyruvic acid and prevent growth of the biomass, the bioconversion medium must contain neither Fe ions nor thiamine.

In fact in the method of the invention, the culture is effected in such a way as to produce pyruvic acid and not to develop Candida type cells and it therefore not necessary to add Fe ions and thiamine which favors the development of these cells.

By way of example of a culture medium able to be used, it is possible to use aqueous solutions comprising solely glucose or starch hydrolyzate, nitrate of ammonium, potassium monophosphate, magnesium sulphate and copper ions.

According to a preferred embodiment of the invention, the method for producing pyruvic acid by fermentation comprises the following successive stages:

(a) producing Candida type cells by aerobic culture in a culture medium comprising at least 0.2 g/l of cells, carbon and nitrogen sources, mineral salts and the thiamine required to develop cells at a pH of 4.5 to 5.5, until a cell concentration in the culture medium of at least 5 g/l is obtained.

(b) separating and washing of the cells produced in stage (a), (c) aerobic culture of the cells separated in stage (b) in a bioconversion medium comprising a carbon source, mineral salts, but comprising no thiamine or iron, at a pH of 3.5 to 4.5 with a cell concentration of the culture medium at the start of the culture of at least 5 g/l, and (d) extracting the pyruvic acid from the culture medium.

In this preferred embodiment, the first stage consists of developing the Candida type cells so as to obtain the desired cell concentration by using a culture medium and a pH favorizing the growth of these cells. Once the quantity of required cells is obtained, the latter are separated from the culture medium and are washed by means of a culture medium, such the one to be used in the next stage (c); in this stage, the choice of the culture conditions is directed towards producing pyruvic acid. Therefore, the pH is from 3.5 to 4.5 and preferably 4, and a bioconversion medium is used comprising carbon, but no thiamine or iron. During this stage, the pyruvic acid accumulates in the bioconversion medium and is extracted by means of conventional methods, for example by first of all separating the pyruvic acid from the cells by ultrafiltration, and then the pyruvic acid from the alpha-ketoglutaric acid by placing it in contact with an ion-exchanger resin.

Generally, this continuous process is used in an installation comprising a fermentor connected to the ultrafiltration cell. Thus, after the cells have grown during the first phase, said cells can be separated from the culture medium in the ultrafiltration cell and also the separated cells are washed by gradually changing the culture medium by diafiltration. The culture at a pH of 3.5 to 4.5 is then produced by making the culture medium containing the cells circulate between the fermentor and the ultrafiltration cell in order to continuously extract the pyruvic acid produced. The pyruvic acid extracted inside the ultrafiltration cell, together with the culture medium, can be separated onto an ion-exchanger resin.

In this preferred embodiment of the invention, the culture medium used in stage (a) contains sources of carbon and nitrogen, as well as mineral salts. The sources of carbon and nitrogen and the mineral salts used can be those previously mentioned. The nitrogen sources can be organic or inorganic substances, for example ammonium sulphate, nitrate of ammonium, carbamide, peptone or any other peptidic compound. Between two branches resulting in identical bioconversion yields of the pyruvic acid substrate, reasons of the cost of the nitrogen source result in the branch containing mineral nitrogen being selected. In this case, the culture medium also comprises thiamine which can be introduced in a pure form or in the form of an analogous substance or any substance containing thiamine, for example a yeast extract or a corn maceration solution.

Certain culture mediums require the addition of other additives, such as vitamins, methionines, etc., but the use of such additives result in pyruvic acid being obtained at a higher cost.

In stages (a) and (c) of the method according to the invention, the aerobic conditions are obtained by injecting oxygen into the culture medium. In the first stage directed towards the development of the biomass, a quantity of oxygen greater than that of the third (c) stage is used and directed towards producing pyruvic acid. In both cases, the culture medium is agitated.

BRIEF DESCRIPTION OF THE DRAWINGS

Other characteristics and advantages of the invention shall be more readily understood on reading the following description with reference to the annexed drawing in which.

DETAILED DESCRIPTION OF THE PREFERRED EMBODIMENTS

Figure 1:
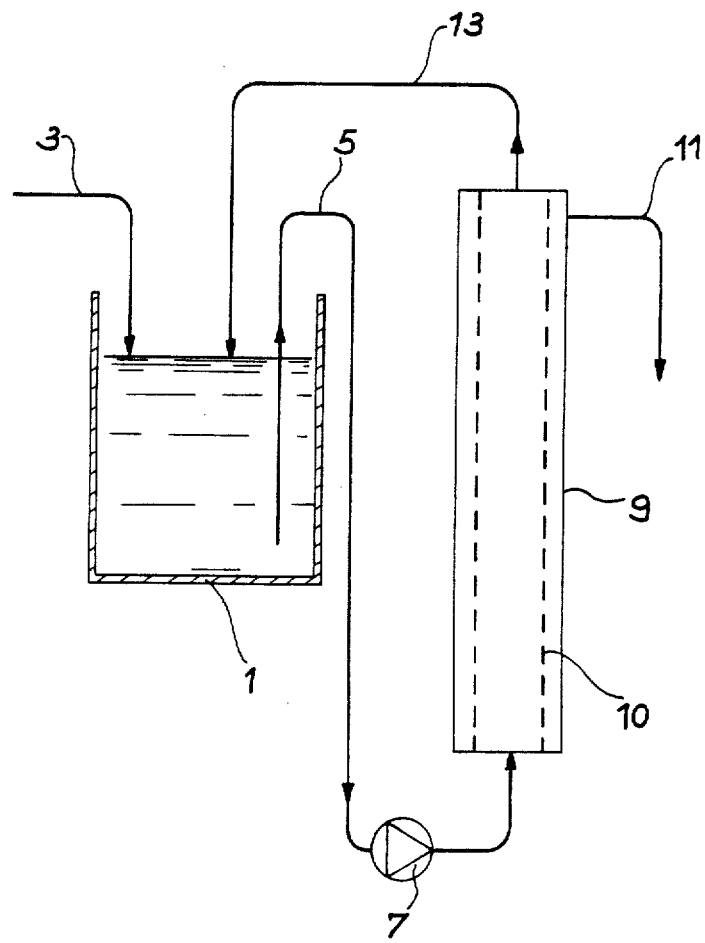
FIG. 1 diagrammatically shows an installation for implementing the method according to the invention.

As illustrated in FIG. 1, it can be seen that the installation allowing for implementation of the method of the invention comprises one fermentor 1 provided with feeding means 3 of products required for fermentation, and means not shown on the drawing relating to temperature adjustment, pH adjustment and oxygen admission and agitation.

The medium in the fermentor can be sucked up by the conduit 5 equipped with a pump 7 so as to be circulated inside an ultrafiltration device 9 equipped with filtering walls 10 from which the ultrafiltered liquid medium is extracted, which in particular comprises the pyruvic acid and the alpha-ketoglutaric produced at the time of fermentation. The cell-enriched culture medium leaving the ultrafiltration device 9 is recycled by means of the conduit 13 inside the fermentor 1.

In order to implement the method for producing pyruvic acid according to the invention, the following operation is carried out:

Stage (a): production of cells

This first stage is embodied by first inserting inside the fermentor a culture medium C1 having the following composition:

glucose: 50 g/l,
$NH_4NO_3$: 2.5 g/l,
$MgSO_4$: 1 g/l,
$KH_2PO_4$: 2 g/l,
$Fe^{2+}$: $2.10^{-6}$ g/l,
$Cu^{2+}$: $2.10^{-6}$ g/l
meat extract: 0.2 g/l
thiamine: $10^{-6}$ g/l to which added is 0.2 g/l of the Candida Lipolytica type cells.

The culture is then embodied in the following conditions:

pH: 5
Temperature: 30° C. ±3° C.,
partial pressure of dissolved oxygen: 80%±10% of the saturation pressure of the oxygen inside the culture medium at 30° C.,
agitation: 250 to 950 rpm (for a Reynolds of 8500 to 32000).

The culture is continued for 90 hrs by roughly keeping the culture conditions constant.

At the end of the operation, the concentrations of the cells and the pyruvic acid and alpha-ketoglutaric acid concentrations of the culture medium are determined. The results obtained are as follows:

cells: 5 to 15 g/l
pyruvic acid: 10 to 15 g/l
alpha-ketoglutaric acid: 5 to 8 g/l.

Stage (b): Separation of cells by ultrafiltration, washing of cells and change of culture medium by diafiltration So as to embody this stage, the pump 7 is started and the culture medium containing the cells is made to circulate inside the ultrafiltration device 9, which includes Carbosep brand filtering membranes, constituted by a porous carbon support covered with a zirconium oxide microporous coating.

The culture medium is made to circulate at a tangential speed of 4±2 m/s. During this passage inside the ultrafiltration device, the medium is impoverished of liquid. In a first phase, the *Candida Lypolytica* cells are concentrated in ¼ of the initial volume of the culture medium.

In a second phase, the culture medium C2 is introduced into the ultrafiltration device by means of the conduit 3, said culture C2 to be used in the next pyruvic acid production stage and which has the following composition:

glucose: 100 g/l,
$NH_4NO_3$: 5 g/l,
$KH_2PO_4$: 2 g/l,
$MgSO_4$: 1 g/l,
$Cu^{2+}$: $2.10^{-6}$ g/l, so as to bring back the volume of the culture medium from V/4 to V/2. This addition is then interrupted and the culture medium is again concentrated from V/2 to V/4 by drawing off the liquid by means of the conduit 11. These three adding operations of the second culture medium C2 are renewed so as to pass from V/4 to V/2. In a final phase, the second culture medium C2 is added to bring the culture medium volume circulating inside the fermentor from V/4 to V. This medium then contains 5 to 10 g/l of cells and the third stage C can then be embodied.

Stage (c): Production of pyruvic acid

The culture of cells is carried out in the following conditions:
pH: 4,
temperature: 30° C.±3° C.,
partial oxygen pressure: 50%,
Agitation: 700 rpm (for a Reynolds of 500), and during the entire period of the culture, the culture conditions and the composition of the culture medium are kept roughly constant.

During this pyruvic acid production, the culture medium passes into the ultrafiltration device and, by means of the conduit 11, the liquid containing the pyruvic acid, the alpha-ketoglutaric acid and other products are continuously extracted. The acid present in this liquid is recuperated by placing it in contact with a quaternary ammonium type ion-exchanger resin, such as Duolite, A162 resin, and the liquid and cells are recycled by the conduit 13 in the fermentor 1.

After 90 hrs of culture, the concentrations of the cells, pyruvic acid and the alpha-ketoglutaric acid of the culture medium are determined. By way of example, one of the results obtained is the following:
pyruvic acid: 40.63 g/l,
alpha-ketoglutaric acid: 5.90 g/l,
cells: 6.0 g/l.

Thus, it shall be observed that, by usng in this stage (c) a pH of 4 instead of a pH of 5 and a culture medium containing no thiamine, no $Fe^{2+}$ ions and no meat extract, it is then possible to increase the production of pyruvic acid by decreasing the production of alpha-ketoglutaric acid of keeeing the amount of cells of the culture medium to a virtually constant value.

Figure 2:
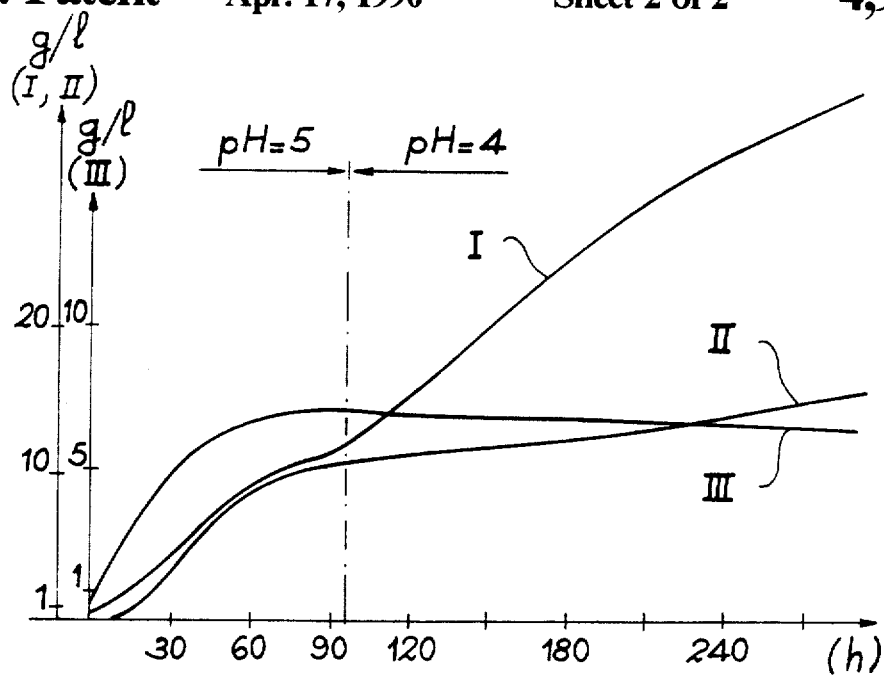
FIG. 2 is a diagram illustrating the variations of the quantity of pyruvic acid produced (curve I), the quantity of alpha-ketoglutaric acid produced (curve II), and the evolution of the biomass concentration (curve III) according to the period of culture when the latter is embodied with a change of the culture pH from 5 to 4 at the end of 90 hours.

FIG. 2 shows the concentration variations (in g/l) of the pyruvic acid (curve I), alpha-ketoglutaric acid (curve II) and the cells (curve III) of the culture medium according to the culture period (in hours) effected in the conditions previously described with a change of medium and pH at the end of 90 hrs.

This figure shows that the pyruvic acid and alpha-ketoglutaric acid production is roughly the same at the start of the culture, namely in stage (a) at pH 5, and, from the time the pH and medium are changed, namely in stape (c) at pH 4, the production of pyruvic acid increases more significantly than the production of alpha-ketoglutaric acid. The production of Candida type cells increases in stage (a) until a change of the pH and the medium and it becomes almost constant resulting from this change of medium.

Therefore, the method of the invention makes it possible to increase the production of pyruvic acid with respect to that of alpha-ketoglutaric acid, and this is extremely advantageous for exploitation on an industrial scale.

The following table shows the carbon results during production of the cells (stage a) and during production of the pyruvic acid (stage c).

TABLE

| GLUCOSE | RESULTS IN C (g) | |
|---|---|---|
| | STAGE (a) +20 | Stage (c) +40 |
| Cells | 3 | 0 |
| Pyruvic acid | 6.2 | 16.4 |
| Alpha-ketoglutaric acid | 2.6 | 2 |
| $CO_2$ (and others) | 8.2 | 21.6 |
| | 20 | 40 |

In the light of these results, it is shown that, although there is twice as much carbon in stage (c), the production of alpha-ketoglutaric acid is less than in stage (a). On the other hand, the pyruvic acid bioconversion yield is clearly more significant in stage (c) than in stage (a).

In another series of experiments, the stage c culture medium was used and a bioconversion was embodied in the same conditions as those previously described as regards stage (c) for 90 hrs, but by using pHs ranging from 3 to 9. At the end of the operation, on each occasion the alpha-ketoglutaric acid and pyruvic acid concentrations of the culture medium were determined.

Figure 3:
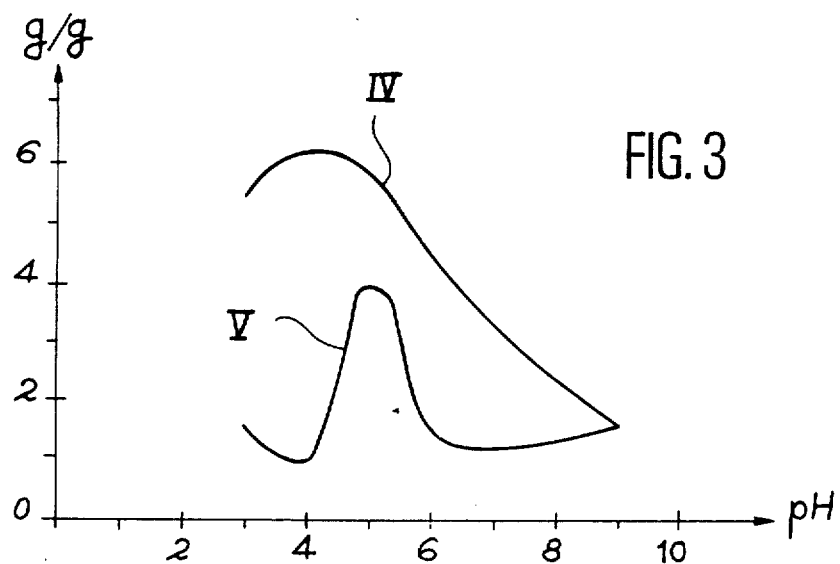
FIG. 3 is a diagram representing the production of pyruvic acid (curve IV) and alpha-ketoglutaric acid (curve V) per gram of glucose consumed, according to the pH of the bioconversion medium.

FIG. 3 illustrates the results obtained. This figure also shows in ordinates the amount of pyruvic acid produced (in gram per gram of glucose introduced) and the amount of alpha-ketoglutaric acid produced (in gram per gram of glucose introduced). The curve IV relates to the pyruvic acid and the curve V to the alpha-ketoglutaric acid.

This figure shows that the production of pyruvic acid passes through a maximum to 4 pH. On the other hand, the curve V which relates to the production of the alpha-ketoglutaric acid passes through a highly-pronounced maximum to a pH of 5 and has a minimum of a pH of 4.

Thus, the use in the invention of a pH equal to 4 for the production of pyruvic acid makes it possible to limit the production of alpha-ketoglutaric acid. On the other hand, as for the production of the biomass of cells, which corresponds to stage (a) of the method according to the invention, it preferable to use a pH of about 5.

What is claimed is:

1. A method for producing pyruvic acid by means of fermentation, wherein it consists of:
   1.—cultivating Candida cells in a culture medium comprising a source of carbon, a source of nitrogen, thiamine and mineral salts at a pH of 4.5 to 5.5 in aerobic conditions,
   2.—separating the cells thus produced from the growing medium,
   3.—cultivating said cells in a bioconversion medium containing a source of carbon and mineral elements at a pH of 3.5 to 4.5 in aerobic conditions, and
   4.—extracting the pyruvic acid produced from the culture medium.

2. A method as recited in claim 1, wherein the bioconversion medium comprises no thiamine or iron.

3. A method as recited in claim 1, wherein bioconversion is embodied at a pH of about 4.

4. A method as claimed in claim 1, wherein the cell concentration of the bioconversion medium at the start of the culture is at least 5 g/l.

5. A method for producing pyruvic acid by means of fermentation, wherein it comprises the following successive stages:
   a—production of Candida cells by means of an aerobic culture in a culture medium comprising at the start at least 0.2 g/l of cells, sources of carbon and nitrogen, mineral salts and the thiamine required for developing cells at a pH of 4.5 to 5.5 until a cell concentration in the culture medium of at least 5/1 is obtained, b—separation and washing of cells produced during stage (a), c—aerobic culture of cells separated during stage (b) in a culture medium comprising a source of carbon and mineral salts, but containing neither thiamine nor iron, at a pH of 3.5 to 4.5 with a cell concentration of the bioconversion medium at the start of the culture of at least 5 g/l, and d—extraction of the pyruvic acid from the culture medium.

6. A method as recited in claim 5, wherein the pH is about 5 in stage (a).

7. A method as recited in claim 5, wherein the pH is about 4 in stage (c).

8. A method as recited in claim 5, wherein the separation and washing of the cells produced in stage (c) is effected by means of ultrafiltration and diafiltration.

9. A method as recited in claim 8, wherein the washing medium is the culture medium used in stage (c).

10. A method as recited in claim 5, wherein the pyruvic acid and alpha-ketoglutaric acid produced by fermentation are separated from the cells by means of ultrafiltration, and then the pyruvic acid is separated from the alpha-ketoglutaric acid by means of an ion-exchanger resin.

11. A method as recited in claim 2, wherein bioconversion is embodied at a pH of about 4.

12. A method as claimed in claim 2, wherein the cell concentration of the bioconversion medium at the start of the culture is at least 5 g/l.

13. A method as recited in claim 6, wherein the pH is about 4 in stage (c).

* * * * *